United States Patent [19]

Guillaumet et al.

[11] Patent Number: 5,346,916

[45] Date of Patent: Sep. 13, 1994

[54] ALKOXY-3-[(TOLUENESUL-FONYLAMINOALKYL)AMINO] CHROMAN COMPOUNDS

[75] Inventors: Gérald Guillaumet, Orleans; Béatrice Guardiola, Neuilly Sur Seine, both of France

[73] Assignee: Adir Et Compagnie, Courbevoie, France

[21] Appl. No.: 33,156

[22] Filed: Mar. 16, 1993

Related U.S. Application Data

[62] Division of Ser. No. 959,044, Oct. 9, 1992, which is a division of Ser. No. 677,136, Mar. 29, 1991, Pat. No. 5,252,578.

[30] Foreign Application Priority Data

Apr. 9, 1990 [FR] France .................. 90 04481

[51] Int. Cl.$^5$ .................. A61K 31/385; C07D 335/04
[52] U.S. Cl. .................. 514/434; 514/456; 549/23; 549/404
[58] Field of Search .................. 549/23, 404; 514/434, 514/456

[56] References Cited

U.S. PATENT DOCUMENTS 5,049,564  9/1991  BeBernardis et al. .............. 514/278
5,075,303  12/1991  Cliffe .................. 546/16

FOREIGN PATENT DOCUMENTS 222996  4/1977  European Pat. Off. .
279150  3/1979  European Pat. Off. .

OTHER PUBLICATIONS

Korobov, et al., Chem. Phys. Lett., 45 (1977), p. 498.

*Primary Examiner*—Johann Richter
*Assistant Examiner*—Catherine S. Kilby Scalzo
*Attorney, Agent, or Firm*—Gordon W. Hueschen

[57] ABSTRACT

The invention relates to compounds of the formula (I):

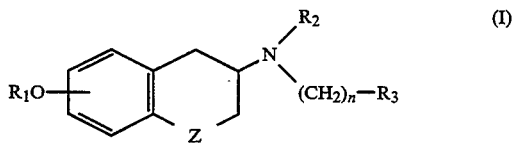

in which:
  Z represents an oxygen atom or a sulfur atom,
  $R_1$ represents a hydrogen atom or an alkyl group,
  $R_2$ represents a hydrogen atom or an alkyl group,
  n is one to six, inclusive,
  $R_3$ represents an amino group, substituted with phenylsulfonyl, and
medicinal products containing the same.

13 Claims, No Drawings

ALKOXY-3-[(TOLUENESULFONYLAMINOALKYL)AMINO] CHROMAN COMPOUNDS

The present invention is a division of our prior-filed copending U.S. application Ser. No. 07/959,044, filed Oct. 9, 1992, in turn a division of Ser. No. 07/677,136, filed Mar. 29, 1991, now U.S. Pat. No. 5,252,578.

The present invention relates to new 3-aminochroman compounds, to a process for preparing these and to pharmaceutical compositions containing them.

3-Aminochromans and 3-aminothiochromans are known to be ligands for central nervous system receptors which are useable especially, as ligands for serotonin receptors, in the treatment of disorders of the central nervous system, depression and anxiety.

Aminochroman and aminothiochroman compounds have, for example, been described in European patents EP 279,150 and EP 222,996. The compounds described in these patents display some affinity for 5-HT$_{1A}$ receptors, but also for D$_2$ receptors, which leads to very low selectivity. A factor of 10 separates the 5-HT$_{1A}$ affinities relative to those for D$_2$. In contrast, the compounds of the present invention, which are 3-aminochroman and 3-aminothiochroman compounds, apart from the fact that their structures are new, possess exceptional pharmacological properties. In effect, they are very potent ligands for 5-HT$_{1A}$ receptors. This very strong affinity is all the more advantageous for the fact that it is backed up by a very great selectivity with respect to these receptors relative to D$_2$ and α$_2$ receptors. The affinity of the compounds of the invention with respect to 5-HT$_{1A}$ receptors is 10$^2$-fold and 10$^4$-fold greater, respectively, than that observed for D$_2$ and α$_2$ receptors. These exceptional pharmacological properties render the compounds of the present invention useable in the treatment of afflictions of the central nervous system, especially of the serotoninergic system, such as depression, anxiety, stress, schizophrenia and pain, and also in the treatment of hypertension and the prevention of atheroma and as an agent modifying feeding and sexual behavior.

More specifically, the present invention relates to the compounds of general formula (I):

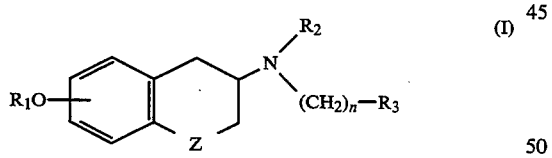

in which:

Z represents an oxygen atom or a sulfur atom,
R$_1$ represents a hydrogen atom or a linear or branched (C$_1$–C$_6$) alkyl group,
R$_2$ represents a hydrogen atom or a linear or branched (C$_1$–C$_6$) alkyl group,
n is an integer between 1 and 6,
R$_3$ represents a nitrile group or an amino group optionally substituted with:
  a linear or branched acyl group comprising 2 to 7 carbon atoms,
  an alkylsulfonyl group,
  an arylsulfonyl group optionally substituted with an alkyl, alkoxy or hydroxyl group or a halogen atom,
  one or two linear or branched (C$_1$–C$_6$) alkyl groups, or R$_3$ represents any one of the following groups:

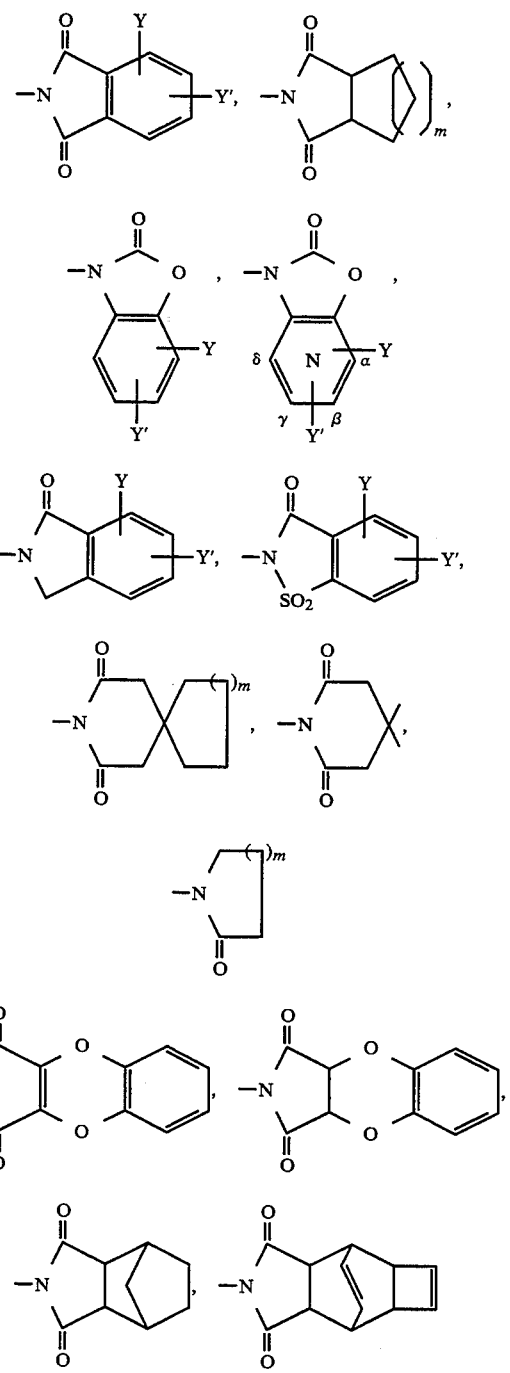

in which:

Y and Y', which may be identical or different, represent a hydrogen atom, a halogen atom or an alkyl, alkoxy or hydroxyl group,
m is an integer equal to 1 or 2,
and the nitrogen of the pyridine ring is situated in the α-, β-, γ- or δ-position with respect to the ring-junction, their enantiomers, diastereoisomers and epimers as well as their addition salts with a pharmaceutically acceptable acid.

Among pharmaceutically acceptable acids, hydrochloric, sulfuric, tartaric, maleic, fumaric, oxalic, methanesulfonic and camphoric acids, and the like, may be mentioned without implied limitation.

The invention also encompasses the process for preparing the compounds of general formula (I), wherein there is used as a starting material: either a compound of formula (II):

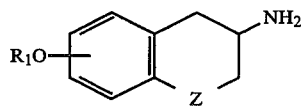
(II)

in which $R_1$ and Z have the same meaning as in the formula (I), which is reacted with a compound of formula (III):

$R_3$—$(CH_2)_n$—X (III)

in which $R_3$ and n have the same meaning as in the formula (I) and X is a halogen atom, to lead to a compound of formula (I/a), a special case of the compounds of formula ( I ):

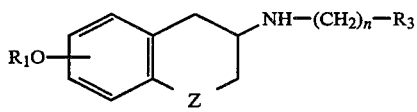
(I/a)

in which $R_1$, $R_3$, Z and n have the same meaning as in the formula (I), which is optionally subjected to the action of a compound of formula (IV):

$R'_2$—X (IV)

in which $R'_2$ represents a linear or branched ($C_1$-$C_6$) alkyl group and X represents a halogen atom, to lead to a compound of formula (I/b), a special case of the compounds of formula (I):

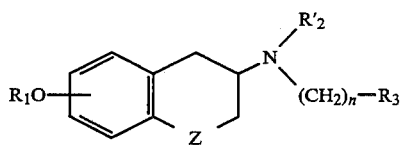
(I/b)

in which $R_1$, Z, $R'_2$, $R_3$ and n are defined as above, or b a compound of formula (V):

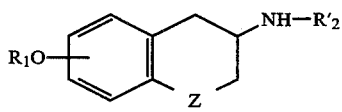
(V)

in which $R_1$, Z and $R'_2$ have the same meanings as above, which is reacted:
either with a compound of formula (III):

$R_3$—$(CH_2)_n$—X (III)

in which $R_3$, n and X are defined as above, to lead to a compounds of formula (I/b), a special case of the compounds of formula (I):

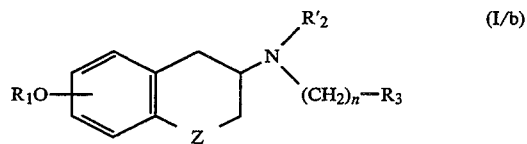
(I/b)

in which $R_1$, Z, $R'_2$, $R_3$ and n are defined as above, or with a compound of formula (III/a):

NC—$(CH_2)_m$—X (III/a)

in which X has the same meaning as above and m is an integer between 1 and 3, to lead to a compound of formula (I/c), a special case of the compounds of formula (I):

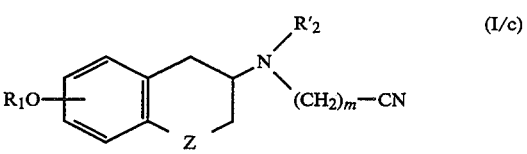
(I/c)

in which $R_1$, Z, $R'_2$ and m are defined as above, which is reduced catalytically in the presence of Raney nickel and ammonia, or chemically with lithium aluminum hydride or with sodium in alcohol, to lead to the compound of formula (I/d), a special case of the compounds of formula (I):

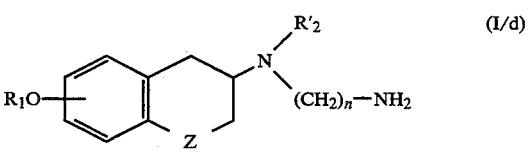
(I/d)

in which $R_1$, Z, $R'_2$ and n are defined as above, which is reacted:
either with a compound of formula (VI/A):

$R_{4A}$—$SO_2$—X (VI/A)

in which $R_{4A}$ is an alkyl group or an aryl group optionally substituted with an alkyl group and X is a halogen atom, to lead to a compound, of formula (I/e), a special case of the compounds of formula (I):

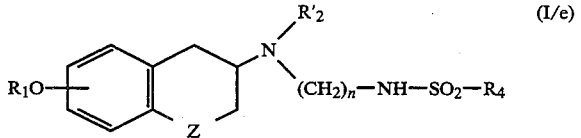
(I/e)

in which $R_1$, Z, $R'_2$, $R_4$ and n are defined as above, or with a compound of formula (VI/B):ps
$R_{4B}$—CO—T (VI/B)

in which $R_{4B}$ represents a linear or branched alkyl group having 1 to 6 carbon atoms and T a leaving group selected from halogen and lower alkoxy, or a compound of formula (VI/C):

$R_{4B}$—CO—O—CO—$R_{4B}$ (VI/C)

in which $R_{4B}$ has the same definition as above, to lead to a compound of formula (I/F):

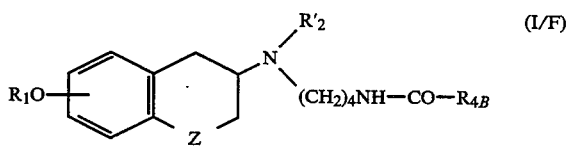

in which $R_1$, $Z$, $R'_2$, $R_{4B}$ and n have the same definition as above, a special case of the compounds of formula (I) for which $R_3$ represents an amino group substituted with a linear or branched acyl group having two to seven carbon atoms, or c a compound of formula (VII):

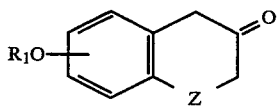

in which $R_1$ and $Z$ have the same meaning as in the formula (I), which is subjected to a reductive amination in the presence of a compound of formula (VIII):

in which $R_2$, $R_3$ and n are defined as in the formula (I), to lead to a compound of formula (I) which, when $R_2$ represents a hydrogen atom, may be subjected to the action of a compound of formula (IV):

in which $R'_2$ and X are defined as above, to lead to a compound of formula (I/b), a special case of the compounds of formula (I):

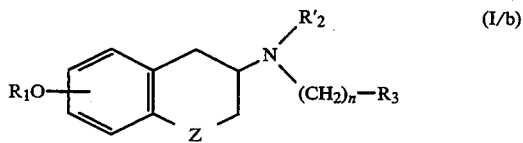

in which $R_1$, $Z$, $R'_2$, $R_3$ and n are defined as above, or alternatively d a compound of formula (IX):

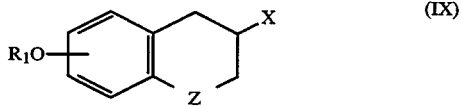

in which $R_1$ and $Z$ have the same meaning as in the formula (I) and X is a halogen atom, which is subjected to the action of a derivative of formula (X):

in which n and $R_3$ are defined as above, to lead to a compound of formula (I/a), a special case of compounds of formula (I):

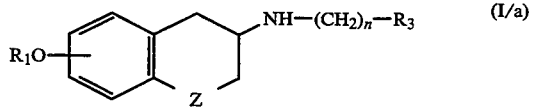

in which $R_1$, $Z$, n and $R_3$ are defined as above, which is optionally subjected to the action of a compound of formula (IV):

in which $R'_2$ and X are defined as above, to lead to a compound of formula (I/b), a special case of the compounds of formula (I):

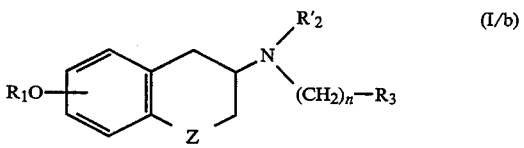

in which $R_1$, $Z$, $R'_2$, $R_3$ and n are defined as above, which compounds of formula (I/a), (I/b), (I/c), (I/d) and (I/e) are optionally separated into their isomers according to a conventional separating technique, which are purified by a conventional purification technique and which are convened, if so desired, to their addition salts with a pharmaceutically acceptable acid.

The compounds of formula (I) possess very advantageous pharmacological properties.

Binding tests showed that the compounds of the invention behave as very potent ligands for 5-$HT_{1A}$ receptors, with an agonist or antagonist activity at central nervous system level. This very great affinity is accompanied by a very great selectivity with respect to these receptors relative to $D_2$ and $\alpha_2$ receptors.

The compounds of the invention hence find their application in the treatment of stress, anxiety, depression, schizophrenia and pain, cardiovascular diseases and hypertension. They can also modify feeding and sexual behavior.

The subject of the present invention is also pharmaceutical compositions containing as active principle at least one compound of general formula (I) or one of its addition salts with a pharmaceutically acceptable acid, alone or in combination with one or more non-toxic, inert excipients or vehicles.

Among the pharmaceutical compositions according to the invention, there may be mentioned more especially those which are suitable for oral, parenteral or nasal administration, simple or sugar-coated tablets, sublingual tablets, sachets, packets, hard gelatin capsules, sublingual preparations, troches, suppositories, creams, ointments, skin gels, and the like.

The dosage varies according to the patient's age and weight and the nature and severity of the condition, as well as the administration route. The latter can be oral, nasal, rectal or parenteral.

Generally speaking, an individual dosage ranges between 0.1 and 100 mg for a treatment in 1 to 3 doses per 24 hours.

The examples which follow illustrate the invention and in no way limit it.

EXAMPLE 1

3-[N-(4-phthalimidobutyl)amino]-5-methoxychroman

In a round bottomed flask, 2.2 mmol of 3-amino-5-methoxychroman (described in Patent EP 279,150) are dissolved in 6 ml of dimethylformamide in the presence of 2.4 mmol of N-(4-bromobutyl)phthalimide, 6.6 mmol of potassium carbonate and a catalytic amount of potassium iodide. The mixture is left stirring at 60° C. for 6 hours. After cooling, the solvent is evaporated off and, after aqueous hydrolysis, the crude reaction mixture is extracted with dichloromethane. After washing, drying and evaporation of the organic phase, the expected product is obtained after purification by chromatography on a silica column (elution solvent: ether/petroleum ether, 5:95).

the solvent is evaporated off and the crude reaction mixture is taken up with 10 ml of water and extracted with dichloromethane. The organic phase is dried and evaporated and the expected product is obtained after purification by chromatography on a silica column (elution solvent: ether/petroleum ether, 1:99).

Yield: 81%

Proton nuclear magnetic resonance: (CDCl$_3$):

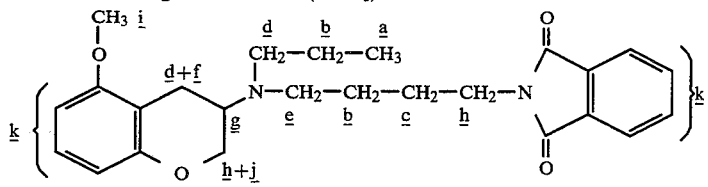

<u>a</u>  $\delta$ = 0.88 ppm (3H,t)
<u>b</u>  $\delta$ = 1.48 ppm (4H,m)
<u>c</u>  $\delta$ = 1.72 ppm (2H,m)
<u>d</u>  $\delta$ = 2.50 ppm (3H,m)
<u>e</u>  $\delta$ = 2.60 ppm (2H,m)
<u>f</u>  $\delta$ = 2.88 ppm (1H,dd)
<u>g</u>  $\delta$ = 3.12 ppm (1H,m)
<u>h</u>  $\delta$ = 3.70 ppm (3H,m)
<u>i</u>  $\delta$ = 3.80 ppm (3H,s)
<u>j</u>  $\delta$ = 4.24 ppm (1H,m)
<u>k</u>  $\delta$ between 6.42 and 7.84 ppm (7H,m)

Yield: 67%

Proton nuclear magnetic resonance: (CDCl$_3$):

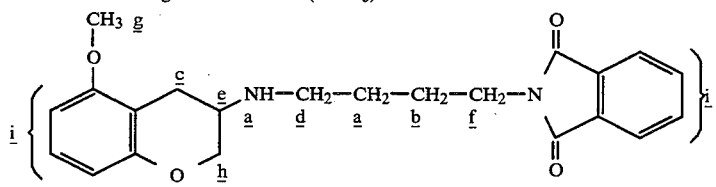

<u>a</u>  $\delta$ = 1.56 ppm (3H,m)
<u>b</u>  $\delta$ = 1.75 ppm (2H,m)
<u>c</u>  $\delta$ between 2.47 and 2.92 ppm (2H,dd)
<u>d</u>  $\delta$ = 2.75 ppm (2H,t)
<u>e</u>  $\delta$ = 3.09 ppm (1H,m)
<u>f</u>  $\delta$ = 3.62 ppm (2H,t)
<u>g</u>  $\delta$ = 3.80 ppm (3H,s)
<u>h</u>  $\delta$ between 3.84 and 4.13 ppm (2H,m)
<u>i</u>  $\delta$ between 6.42 and 7.83 ppm (7H,m)

EXAMPLE 2

3-[N-propyl-N-(4-phthalimidobutyl)amino]-5-methoxychroman 1.5 mmol of the compound prepared in Example 1 is dissolved in 10 ml of dimethylformamide in the presence of 4.4 mmol of 1-iodopropane and 4.4 mmol of potassium carbonate. After 24 hours' stirring at 60° C.,

EXAMPLE 3

3-[N-(3-phthalimidopropyl)amino]-5-methoxychroman

Using the procedure described in Example 1, but replacing N-(4-bromobutyl)phthalimide by N-(3-bromopropyl)phthalimide, the expected product is obtained.

Yields 70%

Proton nuclear magnetic resonance: (CDCl$_3$):

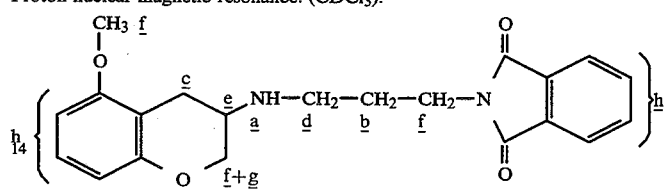

a  δ = 1.56 ppm (1H,s)
b  δ = 1.87 ppm (2H,m)
c  δ between 2.44 and 2.90 ppm (2H,dd)
d  δ = 2.79 ppm (2H,m)
e  δ = 3.06 ppm (1H,m)
f  δ = 3.78 ppm (6H,m)
g  δ = 4.12 ppm (1H,m)
h  δ between 6.40 and 7.83 ppm (7H,m)

EXAMPLE 4

3-[N-propyl-N-(3-phthalimidopropyl)amino]-5-methoxychroman

Using the procedure described in Example 2, but replacing the compound of Example 1 by the compound of Example 3, the expected product is obtained.
Yield: 76%

Proton nuclear magnetic resonance: (CDCl₃):

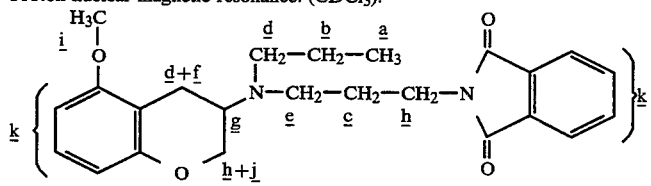

a  δ = 0.90 ppm (3H,t)
b  δ = 1.46 ppm (2H,m)
c  δ = 1.81 ppm (2H,m)
d  δ = 2.50 ppm (3H,m)
e  δ = 2.64 ppm (2H,m)
f  δ = 2.82 ppm (1H,dd)
g  δ = 3.10 ppm (1H,m)
h  δ = 3.72 ppm (3H,m)
i  δ = 3.79 ppm (3H,s)
j  δ = 4.23 ppm (1H,m)
k  δ between 6.40 and 7.83 ppm (7H,m)

EXAMPLE 5

3-[N-(2-phthalimidoethyl)amino]-5-methoxychroman

Using the procedure described in Example 1, but replacing N-(4-bromobutyl)phthalimide by N-(2-bromoethyl)phthalimide, and leaving stirring for 40 hours, the expected product is obtained.
Yield: 30%

Proton nuclear magnetic resonance: (CDCl₃):

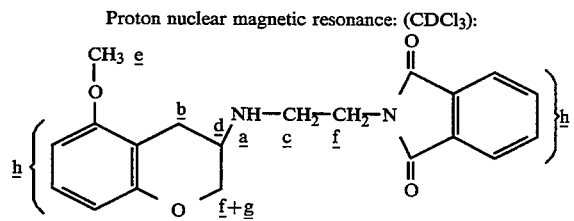

a  δ = 1.48 ppm (1H,s)
b  δ between 2.44 and 2.88 ppm (2H,m)
c  δ = 3.03 ppm (2H,m)
d  δ = 3.15 ppm (1H,m)
e  δ = 3.78 ppm (3H,s)
f  δ = 3.81 ppm (3H,m)
g  δ = 4.1 ppm (1H,m)
h  δ between 6.40 and 7.85 ppm (7H,m)

EXAMPLE 6

3-[N-propyl-N-(2-phthalimidoethyl)amino]-5-methoxychroman

Using the procedure described in Example 2, but replacing the compound of Example 1 by the compound of Example 5, the expected product is obtained.
Yield: 70%

Proton nuclear magnetic resonance: (CDCl₃):

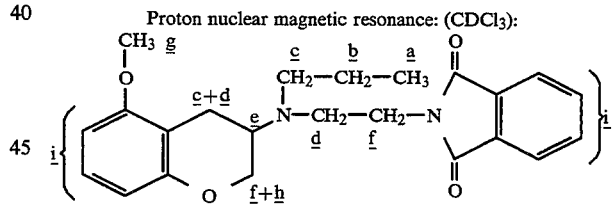

a  δ = 0.79 ppm (3H,t)
b  δ = 1.40 ppm (2H,m)
c  δ = 2.50 ppm (3H,m)
d  δ = 2.84 ppm (3H,m)
e  δ = 3.19 ppm (1H,m)
f  δ = 3.71 ppm (3H,m)
g  δ = 3.79 ppm (3H,s)
h  δ = 4.15 ppm (1H,m)
i  δ between 6.40 and 7.83 ppm (7H,m)

EXAMPLE 7

3-{4-[N-(5-methoxy-3-chromanyl)amino]butyl}-2-oxo-2,3-dihydrooxazolo[4,5-b]pyridine Using the procedure described in Example 1, but replacing N-(4-bromobutyl)phthalimide by N-(4-bromobutyl)-2-oxooxazolo[4,5-b]pyridine and leaving stirring for 48 hours, the expected product is obtained.
Yield: 53%

Proton nuclear magnetic resonance: (CDCl₃):

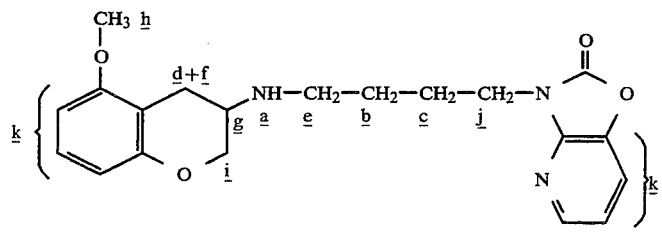

a  δ = 1.34 ppm (1H,s)
b  δ = 1.63 ppm (2H,m)
c  δ = 1.90 ppm (2H,m)
d  δ = 2.48 ppm (1H,dd)
e  δ = 2.78 ppm (2H,m)
f  δ = 2.92 ppm (1H,dd)
g  δ = 3.07 ppm (1H,m)
h  δ = 3.82 ppm (3H,s)
i  δ between 3.84 and 4.14 ppm (2H,m)
j  δ = 3.97 ppm (2H,m)
k  δ between 6.44 and 8.10 ppm (6H,m)

EXAMPLE 8

3-{4-[N-propyl-N-(5-methoxy-3-chromanyl)amino]-butyl}-2-OXO-2,3-dihydrooxazolo[4,5-b]pyridine Using the procedure described in Example 2, but replacing the compound of Example 1 by the compound of Example 5, the expected product is obtained.
Yield: 65%

Proton nuclear magnetic resonance: (CDCl₃):

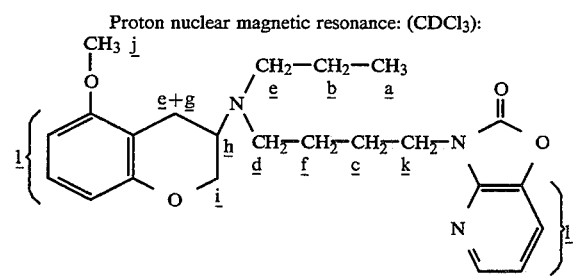

a  δ = 0.84 ppm (3H,t)
b  δ = 1.40 ppm (2H,m)
c  δ = 1.50 ppm (2H,m)
d  δ = 1.85 ppm (2H,m)
e  δ = 2.49 ppm (3H,m)
f  δ = 2.62 ppm (2H,m)
g  δ = 2.83 ppm (1H,m)
h  δ = 3.08 ppm (1H,m)
i  δ = 3.66 and 4.23 ppm (2H,m)
j  δ = 3.81 ppm (3H,s)
k  δ = 3.94 ppm (2H,t)
l  δ between 6.48 and 8.10 ppm (6H,m)

EXAMPLE 9

3-{4-[N-(5-methoxy-3-chromanyl)amino]butyl}-2,4-dioxo-3-azaspiro[4.5]decane

Using the procedure described in Example 1, but replacing N-(4-bromobutyl)phthalimide by N-(4-bromobutyl)-2,4-dioxo-3-azaspiro[4.5]decane and leaving stirring for 24 hours, the expected product is obtained.
Yield: 65%

Proton nuclear magnetic resonance: (CDCl₃):

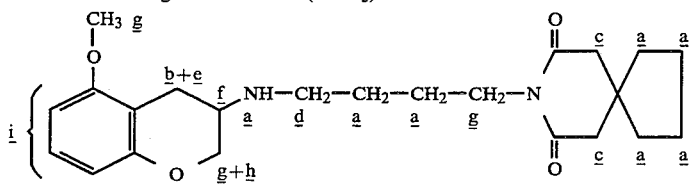

a  δ between 1.45 and 1.85 ppm (13H,m)
b  δ = 2.46 ppm (1H,dd)
c  δ = 2.59 ppm (4H,s)
d  δ = 2.74 ppm (2H,m)
e  δ = 2.92 ppm (1H,dd)
f  δ = 3.05 ppm (1H,m)
g  δ = 3.80 ppm (6H,m)
h  δ = 4.13 ppm (1H,m)
i  δ between 6.41 and 7.04 ppm (3H,m)

Example 10

3{4-[N-propyl-N-(5-methoxy-3-chromanyl)amino]-butyl}-2,4-dioxo-3-azaspiro[4.5]decane Using the procedure described in Example 2, but replacing the compound of Example 1 by the compound of Example 9, the expected product is obtained.

Yield: 72%

Proton nuclear magnetic resonance: (CDCl₃):

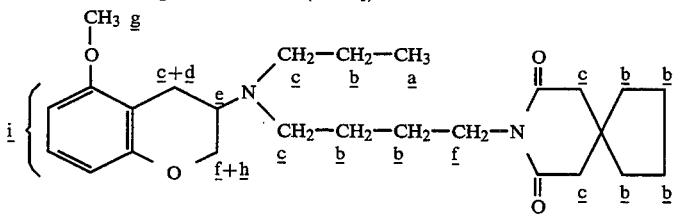

a  δ = 0.87 ppm (3H,t)
b  δ between 1.45 and 1.75 ppm (14H,m)
c  δ = 2.52 ppm (9H,m)
d  δ = 2.84 ppm (1H,m)
e  δ = 3.11 ppm (1H,m)
f  δ = 3.73 ppm (3H,m)
g  δ = 3.81 ppm (3H,s)
h  δ = 4.22 ppm (1H,m)
i  δ between 6.39 and 7.02 ppm (3H,m)

EXAMPLE 11

3-{4-[N-(5-methoxy-3-chromanyl)amino]butyl}-2,4-dioxo-3-azabicyclo[3.3.0]octane

Using the procedure described in Example 1, but replacing N-(4-bromobutyl)phthalimide by N-(4-bromobutyl)-2,4-dioxo-3-azabicyclo[3.3.0]octane and leaving stirring for 24 hours, the expected product is obtained.

Yield: 66%

Proton nuclear magnetic resonance: (CDCl₃):

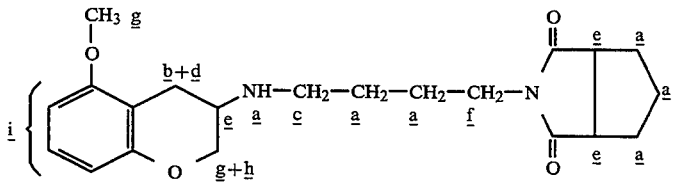

a  δ between 1.18 and 2.19 ppm (11H,m)
b  δ = 2.54 ppm (1H,dd)
c  δ = 2.57 ppm (2H,m)
d  δ = 2.88 ppm (1H,m)
e  δ = 3.29 ppm (3H,m)
f  δ = 3.50 ppm (2H,t)
g  δ between 3.80 and 3.92 ppm (4H,m)
h  δ = 4.35 ppm (1H,m)
i  δ between 6.43 and 7.06 ppm (3H,m)

EXAMPLE 12

3-{4-[N-propyl-N-(5-methoxy-3-chromanyl)amino]-butyl}-2,4-dioxo-3-azabicyclo[3.3.0]octane Using the procedure described in Example 2, but replacing the compound of Example 2 by the compound of Example 11, the expected product is obtained.

Yield: 78%

Proton nuclear magnetic resonance: (CDCl₃):

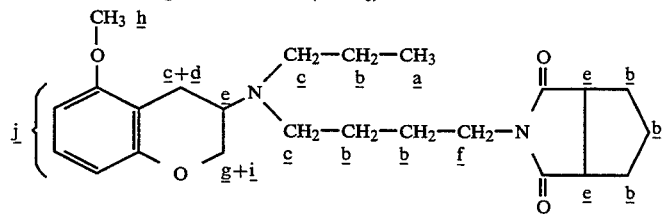

a  δ = 0.88 ppm (3H,m)
b  δ between 1.18 and 2.18 ppm (12H,m)
c  δ = 2.52 ppm (5H,m)
d  δ = 2.84 ppm (1H,dd)
e  δ = 3.12 ppm (3H,m)
f  δ = 3.48 ppm (2H,t)
g  δ = 3.74 ppm (1H,m)
h  δ = 3.82 ppm (3H,s)
i  δ = 4.21 ppm (1H,m)
j  δ between 6.41 and 7.06 ppm (3H,m)

EXAMPLE 13

5-Methoxy-3-[N-propyl-N-cyanomethyl)amino]chroman

In a round-bottomed flask, 6.8 mmol of 3-(N-propylamino)-5-methoxychroman (described in Patent EP 279,150) are dissolved in 10 ml of dimethylformamide in the presence of 20 mmol of chloroacetonitrile, 20 mmol of potassium carbonate and a catalytic amount of potassium iodide. The mixture is stirred at 60° C. for 24 hours. After cooling, the solvent is evaporated off and, after aqueous hydrolysis, the crude reaction mixture is extracted with dichloromethane. After washing, drying and evaporation of the organic phase, the expected product is obtained after purification and chromatography on a silica column (elution solvent: dichloromethane/methanol, 99:1).

Yield: 79%

Proton nuclear magnetic resonance: (CDCl₃):

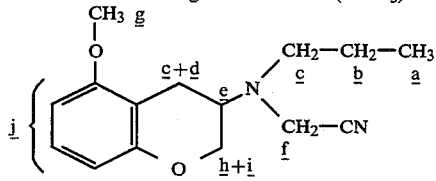

a  δ = 0.92 ppm (3H,t)
b  δ = 1.52 ppm (2H,m)
c  δ = 2.68 ppm (3H,m)
d  δ = 2.98 ppm (1H,dd)
e  δ = 3.10 ppm (1H,m)
f  δ = 3.70 ppm (2H,s)
g  δ = 3.84 ppm (3H,s)
h  δ = 3.91 ppm (1H,m)
i  δ = 4.29 ppm (1H,m)
j  δ between 6.45 and 7.08 ppm (3H,m)

EXAMPLE 14

5-Methoxy-3-[N-propyl-N-(2-aminoethyl)amino]chroman

In a round-bottomed flask, 5.4 mmol of the compound prepared in Example 13 are dissolved in 30 ml of tetrahydrofuran. 11 mmol of LiAlH₄ are added slowly under an inert atmosphere. The reaction mixture is left stirring for 30 minutes at room temperature. 15 ml of ice-cold water are then added to the mixture cooled in ice. The organic phase is then recovered, dried and evaporated and the expected product is obtained after purification by chromatography on a silica column (elution solvent: dichloromethane/methanol, 99:1).

Yield: 72%

Proton nuclear magnetic resonance: (CDCl₃):

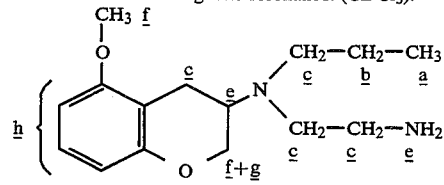

a  δ = 0.89 ppm (3H,t)
b  δ = 1.46 ppm (2H,m)
c  δ between 2.44 and 2.71 ppm (8H,m)
d  δ = 3.14 ppm (1H,m)
e  δ = 3.43 ppm (2H, unresolved complex)
f  δ = 3.80 ppm (4H,m)
g  δ = 4.25 ppm (1H,m)
h  δ between 6.40 and 7.04 ppm (3H,m)

EXAMPLE 15

5-Methoxy-3-{N-propyl-N-[2-(4-toluenesulfonylamino)ethyl]amino}chroman 4 mmol of the compound prepared in Example 14 are dissolved in 30 ml of dichloromethane cooled in ice. 11.4 mmol of triethylamine are added dropwise, followed by 4 mmol of tosyl chloride dissolved in dichloromethane. The mixture is left stirring for 30 minutes at room temperature. The solvent is then evaporated off and the expected product is obtained after purification by chromatography on a silica column (elution solvent: dichloromethane).

Yield: 88%

Proton nuclear magnetic resonance: (CDCl₃):

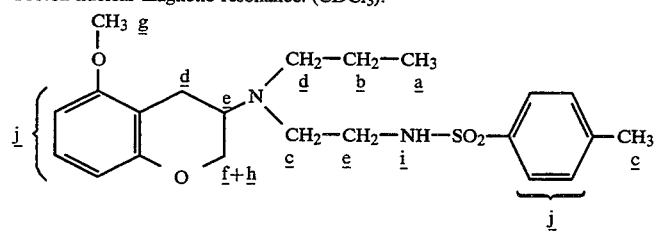

a  δ = 0.76 ppm (3H,t)
b  δ = 1.32 ppm (2H,m)
c  δ = 2.36 ppm (5H,m)
d  δ between 2.48 and 2.52 ppm (4H,m)
e  δ = 2.92 ppm (3H,m)
f  δ = 3.69 ppm (1H,m)
g  δ = 3.82 ppm (3H,s)
h  δ = 4.10 ppm (1H,m)
i  δ = 5.11 ppm (1H, unresolved complex)
j  δ between 6.43 and 7.73 ppm (7H,m)

EXAMPLE 16

5-Methoxy-3-{N-[4-(4,4-dimethyl-2,6-dioxo-1-piperidyl)butyl]amino}chroman

Using the procedure described in Example 1, but replacing N-(4-bromobutyl)phthalimide by N-(4-bromobutyl)-4,4-dimethyl-2,6-dioxopiperidine and leaving stirring for 24 hours, the expected product is obtained.

Yield: 58%

Proton nuclear magnetic resonance: (CDCl₃):

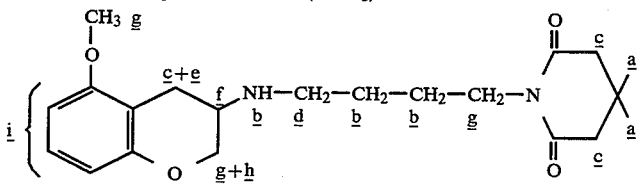

a  δ = 1.06 ppm (6H,s)
b  δ = 1.55 ppm (5H,m)
c  δ = 2.40 ppm (5H,m)
d  δ = 2.70 ppm (2H,m)
e  δ = 2.90 ppm (1H,dd)
f  δ = 3.09 ppm (1H,m)
g  δ = 3.76 ppm (6H,m)
h  δ = 4.17 ppm (1H,m)
i  δ between 6.40 and 7.06 ppm (3H,m)

EXAMPLE 17

5-Methoxy-3-{N-propyl-N[4-(4,4-dimethyl-2,6-dioxo-1-piperidyl)butyl]amino}chroman Using the procedure described in Example 2, but replacing the compound of Example 1 by the compound of Example 16, the expected product is obtained.
Yield: 77%

Proton nuclear magnetic resonance: (CDCl₃):

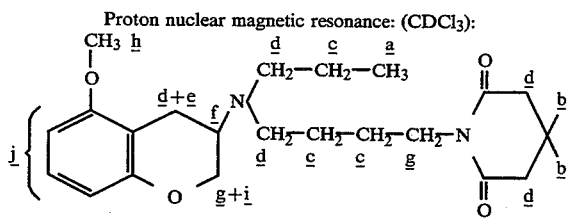

a  δ = 0.88 ppm (3H,t)
b  δ = 1.06 ppm (6H,s)
c  δ = 1.48 ppm (6H,m)
d  δ = 2.52 ppm (9H,m)
e  δ = 2.84 ppm (1H,m)
f  δ = 3.10 ppm (1H,m)
g  δ = 3.75 ppm (3H,s)
h  δ = 3.83 ppm (3H,s)
i  δ = 4.26 ppm (1H,m)
j  δ between 6.42 and 7.05 ppm (3H,m)

EXAMPLE 18

5-Methoxy-3-{N-propyl-N-[3-(4-toluenesulfonylamino)propyl]amino}chroman

Using the procedure described in Example 1, but replacing 3-amino-5-methoxychroman by 3-(N-propylamino)-5methoxychroman and N-(4-bromobutyl)phthalimide by 1-bromo-3-(4-toluenesulfonylamino)propane, and leaving stirring for 72 hours, the expected product is obtained.
Yield: 65%

Proton nuclear magnetic resonance: (CDCl₃):

-continued

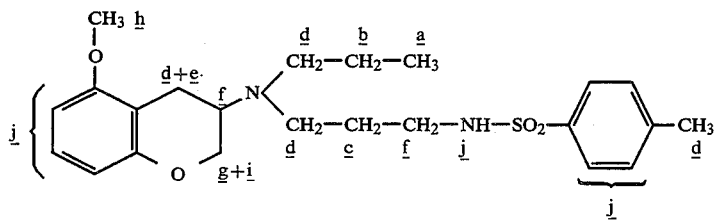

a  δ = 0.88 ppm (3H,t)
b  δ = 1.45 ppm (2H,m)
c  δ = 1.63 ppm (2H,m)
d  δ between 2.40 and 2.70 ppm (8H,m)
e  δ = 2.83 ppm (1H,dd)
f  δ = 3.08 ppm (3H,m)
g  δ = 3.75 ppm (1H,m)
h  δ = 3.83 ppm (3H,s)
i  δ = 4.17 ppm (1H,m)
j  δ between 6.25 and 7.75 ppm (8H,m)

EXAMPLE 19

5-Methoxy-3-[N-propyl-N-(3-cyanopropyl)amino]-chroman

Using the procedure described in Example 13, but replacing chloroacetonitrile by 4-bromobutyronitrile, the expected product is obtained.
Yield: 73 %

Proton nuclear magnetic resonance: (CDCl$_3$):

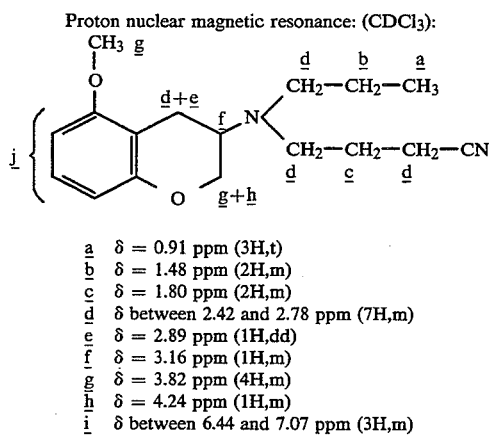

a  δ = 0.91 ppm (3H,t)
b  δ = 1.48 ppm (2H,m)
c  δ = 1.80 ppm (2H,m)
d  δ between 2.42 and 2.78 ppm (7H,m)
e  δ = 2.89 ppm (1H,dd)
f  δ = 3.16 ppm (1H,m)
g  δ = 3.82 ppm (4H,m)
h  δ = 4.24 ppm (1H,m)
i  δ between 6.44 and 7.07 ppm (3H,m)

EXAMPLE 20

5-Methoxy-3-[N-propyl-N-(4-aminobutyl)amino]chroman

Using the procedure described in Example 14, but replacing the compound of Example 13 by the compound of Example 19, the expected product is obtained.

Yield 69%

Proton nuclear magnetic resonance: (CDCl$_3$):

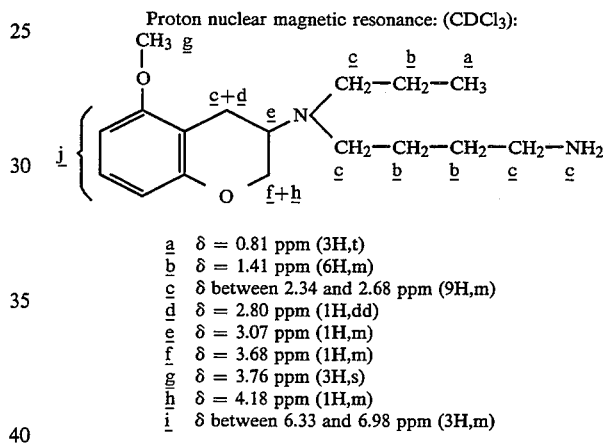

a  δ = 0.81 ppm (3H,t)
b  δ = 1.41 ppm (6H,m)
c  δ between 2.34 and 2.68 ppm (9H,m)
d  δ = 2.80 ppm (1H,dd)
e  δ = 3.07 ppm (1H,m)
f  δ = 3.68 ppm (1H,m)
g  δ = 3.76 ppm (3H,s)
h  δ = 4.18 ppm (1H,m)
i  δ between 6.33 and 6.98 ppm (3H,m)

EXAMPLE 21

5Methoxy-3-{N-propyl-N-[4-(4-toluenesulfonylamino)-butyl]amino}chroman

Using the procedure described in Example 15, but replacing the compound of Example 14 by the compound Example 20, the expected product is obtained.
Yield: 89%

Proton nuclear magnetic resonance: (CDCl$_3$):

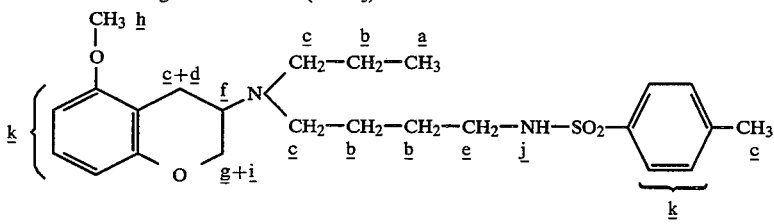

a δ = 0.84 ppm (3H,t)
b δ between 1.35 and 1.57 ppm (6H,m)
c δ between 2.39 and 2.56 ppm (8H,m)
d δ = 2.83 ppm (1H,dd)
e δ = 2.94 ppm (2H,q)
f δ = 3.06 ppm (1H,m)
g δ = 3.73 ppm (1H,m)
h δ = 3.82 ppm (3H,s)
i δ = 4.21 ppm (1H,m)
j δ = 5.51 ppm (3H, unresolved complex)
k δ between 6.41 and 7.75 ppm (7H,m)

EXAMPLE 22

3-{4-[N-propyl-N-(5-methoxy-3-thiochromanyl)amino]butyl}-2,4-dioxo-3-azaspiro[4.5]decane Using the procedure described in Example 10, but replacing 3-amino-5-methoxychroman by 3-amino-5-methoxythiochroman, the expected product is obtained.

EXAMPLE 23

5-Methoxy-3-{N-[4-(3-oxo-2,3-dihydrobenzisothiazol-2yl)butyl]amino}chroman S,S-dioxide Using the procedure described in Example 1, but replacing N-(4-bromobutyl)phthalimide by 3-oxo-2,3-dihydro-2-(4-bromobutyl)benzisothiazole S,S-dioxide and leaving stirring for 24 hours, the product of the title is obtained.

EXAMPLE 24

5-Methoxy-3-{N-n-propyl-N-[4-(3-oxo-2,3-dihydrobenzisothiazol-2-yl)butyl]amino}chroman S,S-dioxide (oxalate)

Using the procedure described in Example 2, but replacing the compound of Example 1 by the compound obtained in Example 23, the expected product is obtained, which product is salified with oxalic acid.

Melting point 85° C. Percentage composition: Calculated: C 57.17 H 5.71 N 4.98 S 5.93 Found: C 56.92 H 5.88 N 5.11 S 5.84

EXAMPLE 25

3-{2-[N-(5-methoxy-3-chromanyl)amino]ethyl}-3-azaspiro[4.5]decane-2,4-dione

Using the procedure described in Example 1, but replacing N-(4-bromobutyl)phthalimide by N-(2-bromobutyl)-2,4-dioxo-3-azaspiro[4.5]decane and leaving stirring for 24 hours, the product of the title is obtained.

EXAMPLE 26

3-{2-[N-n-propyl-N-(5-methoxy-3-chromanyl)amino]ethyl}-3-azaspiro[4.5]decane-2,4-dione (oxalate)

Using the procedure described in Example 2, but replacing the compound of Example 1 by the compound obtained in Example 24, the expected product is obtained, which product is salified with oxalic acid.

Melting point: 56° C.

EXAMPLE 27

3-{4-[N-n-propyl-N-(5-hydroxy-3-chromanyl)amino]butyl}-3-azaspiro[4.5]decane-2,4-dione (oxalate)

The product obtained in Example 10 is treated with the tribromide of a base in methylene chloride at a temperature of −10° C. The product of the title is obtained, which product is salified.

Yield: 60% Melting point: 61° C. Percentage Composition: Calculated: C 62.53 H 7.39 N 5.40 Found C 62.27 H 7.64 N 5.51

EXAMPLE 28

(+)-3-{4-[N-(5-methoxy-3-chromanyl)amino]butyl}-2,4-dioxo-3-azaspiro[4.5]decane oxalate Using the procedure described in Example 9, but replacing 3-amino-5-methoxychroman by (+)-3-amino-5-methoxychroman (obtained by treating 3-amino-5-methoxychroman with (S)-acetyl-(+)-valine in a methanolic medium and filtering the solution obtained, followed by successive crystallizations), the product of the title is obtained.

EXAMPLE 29

(+)-3-{4-[N-n-propyl-N-(5-methoxy-3-chromanyl)amino]butyl}-2,4-dioxo-3-azaspiro[4.5]decane oxalate Using the procedure described in Example 10, but replacing the compound of Example 9 by the compound of Example 28, the product of the title is obtained. It is salified with oxalic acid.

Melting Point: 68° C. Optical rotation, D: +50°

EXAMPLE 30

(−)-3-{4-[N-(5-methoxy-3-chromanyl)amino]butyl}-2,4-dioxo-3-azaspiro[4.5]decane

Using the procedure described in Example 28, but replacing (+)-3-amino-5-methoxychroman by (−)-3-amino-5-methoxychroman (obtained by treating 3-amino-5-methoxychroman with S-acetyl-(−)-valine in a methanolic medium and filtering the solution obtained, followed by successive crystallizations), the product of the title is obtained.

EXAMPLE 31

(-)-3-{4-[N-n-propyl-N-(5-methoxy-3-chromanyl)amino]butyl}-2,4-dioxo-3-azaspiro[4.5]decane oxalate Using the procedure described in Example 29, but replacing the compound of Example 28 by the compound of Example 30, the product of the title is obtained.

Melting point: 68° C. Optical rotation, D: −50°

EXAMPLE 32

(+)-3-{4-[N-(5-methoxy-3-chromanyl)amino]butyl}-2,4-dioxo-3-azabicyclo[3.3.0]octane Using the procedure described in Example 11, but replacing 3-amino-5-methoxychroman by (+)-3-amino-5-methoxychroman, the product of the title is obtained.

EXAMPLE 33

(+)-3-{4-[N-n-propyl-N-(5-methoxy-3-chromanyl-
)amino]butyl}-2,4-dioxo-3-azabicyclo[3.3.0]octane
(oxalate).

The procedure used is that described in Example 12, but replacing the compound of Example 11 by the compound of Example 32. The product is salified with oxalic acid.

Optical rotation $\alpha_D$ of the free amine: +57° (20 mg in 3 ml of CHCl$_3$)

EXAMPLE 34

(−)-3-{4-[N-(5-methoxy-
3-chromanyl)amino]butyl}2,4-dioxo-3-azabicyclo[3.3.0
]octane Using the procedure described in Example 11, but replacing 3-amino-5-methoxychroman by (−)-3-amino-5-methoxychroman, the product of the title is obtained.

EXAMPLE 35

(−)-3-{4-[N-n-propyl-N-(5-methoxy-3-chromanyl-
)amino]butyl}-2,4 -dioxo-3 -azabicyclo[3.3.0 ]octane
oxalate Using the procedure described in Example 12, but replacing the compound of Example 11 by the compound obtained in Example 34, the product of the title is obtained. It is salified with oxalic acid.

Optical rotation $\alpha_D$ of the free amine (20 mg, 3 ml CHCl$_3$): −57°

EXAMPLE 36

5-Methoxy-(+)-3-[N-n-propyl-N-(cyanomethyl-
)amino]chroman

Using the procedure described in Example 13, but replacing 3-amino-5-methoxychroman by (+)-3-amino-5-methoxychroman the product of the title is obtained.

EXAMPLE 37

5-Methoxy-(+)-3-[N-n-propyl-N-(2-aminoethyl-
)amino]chroman

Using the procedure described in Example 14, but replacing the product of Example 13 by the product obtained in Example 36, the product of the title is obtained.

EXAMPLE 38

5-Methoxy-(+)-3-{N-n-propyl-N-[2-(4-toluenesul-
fonylamino)ethyl]amino}chroman (oxalate)

Using the procedure described in Example 15, but replacing the product of Example 14 by the product obtained in Example 37, the product of the title is obtained. It is salified with oxalic acid.

Melting point: 132° C. Optical rotation $\alpha_D$ of the free amine: +44° (20 mg in 3 ml CHCl$_3$)

EXAMPLE 39

5-Methoxy-(−)-3-[N-n-propyl-N-(cyanomethyl-
)amino]chroman

Using the procedure described in Example 13, but replacing 3-amino-5-methoxychroman by (−)-3-amino-5-methoxychroman (obtained in Example 30), the product of the title is obtained.

EXAMPLE 40

5-Methoxy-(−)-3-[N-n-propyl-N-(2-aminoethyl-
)amino]chroman

The procedure used is that described in Example 14, but replacing the product of Example 13 by the product obtained in Example 39; the product of the title is obtained.

EXAMPLE 41

5-Methoxy-(−)-3-{N-n-propyl-N-[2-(4-toluenesul-
fonylamino)ethyl]amino}chroman (oxalate)

Using the procedure described in Example 15, but replacing the product prepared in Example 14 by the product obtained in Example 40, the product of the title is obtained. It is salified with oxalic acid.

Melting point: 132° C.

Optical rotation $\alpha_D$ of the free amine: −44° (20 mg in 3 ml CHCl$_3$)

EXAMPLE 42

5-Methoxy-(+)-3-[N-n-propyl-N-(3-cyanopropyl-
)amino]chroman

Using the procedure described in Example 19, but replacing 3-amino-5-methoxychroman by (+)-3-amino-5-methoxychroman, the product of the title is obtained.

EXAMPLE 43

5-Methoxy-(+)-3-[N-n-propyl-N-(4-aminobutyl-
)amino]chroman

Using the procedure described in Example 20, but replacing the product of Example 19 by the product obtained in Example 42, the product of the title is obtained.

EXAMPLE 44

5-Methoxy-(+)-3-{N-n-propyl-N-[4-(4-toluenesul-
fonylamino)butyl]amino}chroman (oxalate)

Using the procedure described in Example 21, but replacing the product of Example 20 by the product of Example 43, the product of the title is obtained. It is salified with oxalic acid.

Melting point: 95° C. Optical rotation $\alpha_D$ of the free amine: +52° (20 mg in 3 ml CHCl$_3$)

EXAMPLE 45

5-Methoxy-(−)-3-[N-n-propyl-N-(3-cyanopropyl-
)amino ]chroman

Using the procedure described in Example 19, but replacing 3-amino-5-methoxychroman by (−)-3-amino-5-methoxychroman, the product of the titled is obtained.

EXAMPLE 46

5-Methoxy-(−)-3-[N-n-propyl-N-(4-aminobutyl-
)amino]chroman

The procedure used is that described in Example 20, but replacing the product of Example 19 by the product of Example 45; the product of the title is obtained.

EXAMPLE 47

5-Methoxy-(−)-3-{N-n-propyl-N-[4-(4-toluenesulfonylamino)butyl]amino}chroman (oxalate)

Using the procedure described in Example 21, but replacing the product of Example 20 by the product of Example 46, the product of the title is obtained. It is salified by oxalic acid.

Melting point: 95° C. Optical rotation of the free amine: −52° (20 mg in 3 ml of $CHCl_3$)

EXAMPLE 48

N-{2-[N-n-propyl-N-(5-methoxychromanyl)amino]ethyl}acetamide oxalate

In a round-bottomed flask, 17 mmol of the compound prepared in Example 13 are dissolved in 95 ml of tetrahydrofuran. 34 mmol of $LiAlH_4$ are added slowly under an inert atmosphere. The reaction mixture is left stirring for 30 minutes at room temperature. 20 ml of ethyl acetate are then added to the mixture cooled in ice. The mixture is kept stirring for approximately ten minutes and 20 ml of water are then added dropwise. The organic phase is separated and dried over magnesium sulfate. The solvent is evaporated off under reduced pressure and the sample is purified by chromatography on a column using a methylene chloride/methanol mixture. The product is salified with oxalic acid.

Yield: 75% Melting point: 54° C. Spectral characteristics (free base): Infrared: 3280 $cm^1$ ($\nu NH$) Nuclear magnetic resonance: $\delta = 1.96$ ppm, singlet, 3H, $CO-CH_3$

EXAMPLE 49

3-{4-[N-(5-methoxybenzothiopyran-3-yl)amino]butyl}-2,4-dioxo-3-azaspiro[4.5]decane Using the procedure described in Example 9, but replacing 3-amino-5-methoxychroman by 3-amino-3,4-dihydro-5-methoxy-2H-l-benzothiopyran described in Patent Application EP 0,222,996, the product of the title is obtained.

Spectral characteristics: $N(CO-CH_2)_2$: d: 2.59 ppm singlet

EXAMPLE 50

5-Methoxy-3-[N-n-propyl-N-(cyanomethyl)amino]-3,4-dihydro-2H-1-benzothiopyran

Using the procedure described in Example 13, but replacing 3-(N-n-propylamino)-5-methoxychroman by 3-(N-n-propylamino)-5-methoxy-l-benzothiopyran, the product of the title is obtained.

EXAMPLE 51

5-Methoxy-3-[N-n-propyl-N-(2-aminoethyl)amino]-3,4-dihydro-2H-1-benzothiopyran

The procedure used is that described in Example 14, replacing the product of Example 13 by the product obtained in Example 50; the product of the title is obtained.

EXAMPLE 52

5-Methoxy-3-{N-n-propyl-N-[2-(4-toluenesulfonylamino)ethyl]amino}-3,4-dihydro-2H-1-benzothiopyran The procedure used is that described in Example 15, replacing the product of Example 14 by the compound obtained in Example 51.

Spectral characteristics: $^1H$ nuclear magnetic resonance ($CDCl_3$) $\delta = 3.82$ ppm, singlet, 3H, $C_6H_4-CH_3$

EXAMPLE 53

5-Methoxy-3-[N-n-propyl-N-(3-cyanopropyl)amino]-3,4-dihydro-2H-1-benzothiopyran

Using the procedure described in Example 50, but replacing chloroacetonitrile by 4-bromobutyronitrile, the expected product is obtained.

EXAMPLE 54

5-Methoxy-3-[N-n-propyl-N-(4-aminobutyl)amino]-3,4-dihydro-2H-1-benzothiopyran

Using the procedure described in Example 51, but replacing the compound of Example 50 by the compound of Example 53, the product of the title is obtained.

EXAMPLE 55

5-Methoxy-3-{N-n-propyl-N-[4-(4-toluenesulfonylamino)butyl]amino}-3,4-dihydro-2H-1-benzothiopyran Using the procedure described in Example 52, but replacing the compound of Example 51 by the compound obtained in Example 54, the product of the title is obtained.

Spectral characteristics: $^1H$ nuclear magnetic resonance ($CDCl_3$) $\delta = 3.82$ ppm, singlet, 3H, $C_6H_4-CH_3$

EXAMPLE 56

5-Methoxy-3-{N-n-propyl-N-[3-(4-toluenesulfonylamino)propyl]amino}-3,4-dihydro-2H-1-benzothiopyran Using the procedure described in Example 18, but replacing 3-(N-propylamino)-5-methoxychroman by 3-(N -propylamino)-5-methoxy-3,4-dihydro-2H-1-benzothiopyran, the product of the title is obtained.

EXAMPLE 57

N-{2-[N-n-propyl-N-(5-methoxychromanyl)amino]ethyl}isobutyramide

The procedure used is that described in Example 48, but replacing ethyl acetate by ethyl isobutyrate.

By replacing 3 -amino-5 -methoxychroman in the above examples by 3-amino-6-methoxychroman, 3-amino-7-methoxychroman or 3-amino-8-methoxychroman, respectively, or by replacing 3-amino-5-methoxy-3,4-dihydro-2H-1-benzothiopyran by 3-amino-6-methoxy-3,4-dihydro-2H-1-benzothiopyran, by 3-amino-7-methoxychroman or 3-amino-8-methoxychroman, the isomers of Examples Nos. 1 to 56 methoxylated at 6-, 7- or 8-position, respectively, are obtained.

PHARMACOLOGICAL STUDY OF THE DERIVATIVES OF THE INVENTION

EXAMPLE 58

In Vitro Affinity Tests For $5\text{-}HT_{1A}$, $D_2$ and $\alpha_2$ Receptors The in vitro affinity tests for $5\text{-}HT_{1A}$, $D_2$ and $\alpha_2$ receptors were carried out according to conventional binding techniques.

The results of these studies show that the compounds of the invention possess $K_{0.5}$ values of the order of $10^{-10} M$ with respect to $5\text{-}HT_{1A}$ receptors. This very great affinity is complemented by a very great selectivity. In effect, the ratio of the $5\text{-}HT_{1A}/D_2$ affinities is equal to $10^2$; that of the $5\text{-}HT_{1A}/\alpha_2$ affinities is equal to $10^4$.

EXAMPLE 59

Acute Toxicity Study

The acute toxicity was determined after oral administration of increasing doses (0.1, 0.25, 0.50, 0.75 and 1 $g/kg^{-1}$) of the products of the invention to batches of five mice ($20 \pm 2$ grams).

The animals were observed at regular intervals during the first day and daily for two weeks following the treatment. It is apparent that the compounds of the invention are completely non-toxic. No death is observed after the administration of a dose of $1 \text{ g.kg}^{-1}$. No disorder is observed after the administration of this dose.

EXAMPLE 60

$5\text{-}HT_{1A}$ Agonist Activity Lower Lip Retraction Test In Rats

The protocol employed is that described by Berendsen and co-workers (Berendsen H. H. G., Jenck F. and Broekkamp C. L. E. Pharmacology Biochemistry and Behavior 1989, 33, 821–827).

The compounds of the invention are administered to rats which are immediately placed individually in transparent plastic cages ($20 \times 10 \times 10$ cm).

The retraction of the lower lip is noted every fifteen minutes during the three hours following the injection, in the following manner:

0 = lower incisors not visible
1 = lower incisors partially visible
2 = lower incisors completely visible The scores are totaled for each rat and the effect obtained is expressed as a percentage of the maximum possible at three hours.

Six rats are used per group. The experiment is carried out simultaneously on a blind control. The products were administered subcutaneously at doses 0.5, 2 and 8 $\text{mg.kg}^{-1}$.

This test shows that the compounds of the invention have intense $5\text{-}HT_{1A}$ agonist activity.

EXAMPLE 61

Study of the Antidepressant Activity Effect on Escape Failures

The study of the products is carried out on the model of "learned helplessness", which consists in inducing in the animal, by a series of uncontrollable aversive events, a defect during the subsequent avoidance tasks (Martin et al., 1986, Pharmacol. Biochem. Behav., 24, 177–181).

We use male Wistar A. F. rats obtained from CERJ homogeneous breedings, weighing between 180 and 200 grams. The animals are kept in the animal house for one week before the test, in plastic boxes, in groups of 10, at an ambient temperature of $21°\text{ C.} \pm 1°\text{ C.}$, with free access to water and feed.

The animals are isolated in small boxes and subjected to 60 unavoidable electric shocks (0.8 mA every minute $\pm 15$ seconds). A group of control rats does not receive electric shocks. The capacity of the animals to carry out an avoidance learning (shuttle-box) is assessed 48 hours later and during 3 consecutive days. During the learning sections, the animals undergo 2 tests per minute for 15 minutes. The number of escape failures is noted for each rat. The animals are treated (i.p.; 0.5 ml/100 g) 6 hours after the unavoidable shocks and for 4 days thereafter, in the morning 30 minutes before the shuttle-box session and the evening between 6 p.m. and 7 p.m.

The test products are dissolved in distilled water.

The test products are administered at doses of 0.25 mg.kg/day.

The test demonstrates the products of the invention significantly decrease the number of escape failures, thereby reflecting an activity of the antidepressant type.

EXAMPLE 62

Antihypertensive Activity

The animals are acclimatised for a period of six days before the beginning of the study.

At the beginning of the experiment, the rats are anesthetized with 1000 $\text{mg.kg}^{-1}$ of urethane administered intraperitoneally into the jugular vein, introduced with a catheter.

A catheter connected to a precision recorder is placed in the carotid artery. An interval of 10 minutes is allowed to elapse so as to enable the arterial blood pressure to stabilize before the first measurement is taken.

Initially, the solvent is administered intravenously to all animals and the arterial blood pressure is recorded for 30 minutes after the administration, and arterial blood pressure readings are performed 10, 20 and 30 minutes after the administration.

The compounds of the invention are administered in saline solution, also intravenously. Recording of the arterial blood pressure carried out for 30 minutes and pressure measurements are performed 10, 20 and 30 minutes after the administration. The products of the invention bring about a significant decrease in arterial blood pressure.

EXAMPLE 63

Study of the Anxiolytic Activity—Pigeon Conflict Test

Six White Carneaux pigeons not previously used in experiments are trained to peck a Plexiglass key which is transilluminated with red or white light. The response key is mounted on the front wall of the experimental chamber. The pigeons are brought to 85% of their normal weight before the beginning of the experiment, which is carried out using the method of successive approximations (Frester 1953). At the start, each peck of the key (illuminated with a red or white light) which exceeds a force of 0.15N permits access to a mixture of cereals via an automatic dispenser situated under the key. After several days, the cereals are no longer delivered until the 30th peck on the key. When this response to the thirtieth strike is obtained, and when it occurs regularly, permitting the delivery of feed, the color of the light of the key is alternated every three minutes (from white to red and vice versa). The measurement of the level of response to the 30th strike remains operative during each light phase.

During this phase and throughout the experiment, a daily session is composed of 5 cycles of 3 minutes of each light sequence, these sequences being separated by a 30-second pause during which the luminous keys are extinguished and the responses have no effect. Consequently, a sequence lasts approximately 35 to 40 minutes. When these levels of responses are stable and identical for each color during a period of 5 days (this requires 3 to 4 weeks), every 30th response in one of the colored phases simultaneously brings about a release of feed and a brief (200 millisecond) and moderate (1.3 mA) electric shock delivered by electrodes placed on the pubic bones. The level of responses is reduced at first, then returns to the initial level.

The administration of the products of the invention is carried out after a stable level of response is obtained over a period of 5 days.

The intramuscular administration of the products of the invention at a dose of 0.3 mg.kg$^{-1}$ brings about a significant increase in responses whether or not followed by electric shocks, demonstrating the anxiolytic activity of these products.

EXAMPLE 64

Pharmaceutical Composition

Tablets containing 10 mg of (−)-3-{4-[N-propyl-N-(5-methoxy-3-chromanyl)amino]butyl}-2,4-dioxo-3-azaspiro[4.5]decane.

| Formula per 1000 tablets: | |
|---|---|
| (-)-3-{4-[N-Propyl-N-(5-methoxy-3-chromanyl)-amino]butyl}-2,4-dioxo-3-azaspiro[4.5]decane | 10 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

We claim:

1. A compound selected from those of formula (I):

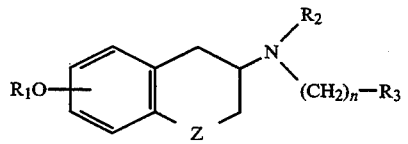

in which:
Z represents oxygen or sulfur,
$R_1$ represents hydrogen or ($C_1$-$C_6$) alkyl,
$R_2$ represents hydrogen or ($C_1$-$C_6$) alkyl,
n is an integer of 1 to 6 inclusive,
$R_3$ represents an amino group substituted with:
an phenylsulfonyl optionally substituted with alkyl, alkoxy, hydroxyl, or halogen,
its enantiomers, diastereoisomers and epimers and its pharmaceutically-acceptable acid addition salts.

2. A compound as claimed in claim 1, wherein $R_1$ is a methyl group.

3. A compound as claimed in claim 1, wherein $R_2$ is an n-propyl group.

4. A compound as claimed in claim 1, wherein $R_1$ is in the 5-position.

5. A compound as claimed in claim 1, wherein $R_2$ is a hydrogen atom.

6. A compound as claimed in claim 1, selected from 5-methoxy-3-{N-propyl-N-[2-(4-toluenesulfonylamino)ethyl]amino}chroman, its isomers and its addition salts with a pharmaceutically-acceptable acid.

7. A compound as claimed in claim 1, selected from 5-methoxy-(+)-3-{N-propyl-N-[2-(4-toluenesulfonylamino)ethyl]amino}chroman, and its addition salts with a pharmaceutically-acceptable acid.

8. A compound as claimed in claim 1, selected from 5-methoxy-(−)-3-{N-propyl-N-[2-(4-toluenesulfonylamino)ethyl]amino}chroman, and its addition salts with a pharmaceutically-acceptable acid.

9. A compound as claimed in claim 1, selected from 5-methoxy-3-{N-n-propyl-N-[4-(4-toluenesulfonylamino)butyl]amino}chroman, its isomers and its addition salts with a pharmaceutically-acceptable acid.

10. A compound as claimed in claim 1, selected from 5-methoxy-(+)-3-{N-n-propyl-N-[4-(4-toluenesulfonylamino)butyl]amino}chroman, and its addition salts with a pharmaceutically-acceptable acid.

11. A compound as claimed in claim 1, selected from 5-methoxy-(−)-3-{N-n-propyl-N-[4-(4-toluenesulfonylamino)butyl]amino}chroman, and its addition salts with a pharmaceutically-acceptable acid.

12. A pharmaceutical composition comprising the active principle as claimed in claim 1, which is useful in the treatment of depression, stress, psychoses, anxiety, pain, schizophrenia, hypertension, or atheroma, and as an agent modifying feeding and sexual behavior, together with a pharmaceutically-acceptable diluent.

13. A method for treating a living animal afflicted with a disorder of the serotoninergic system comprising the step of administering to the said living animal an amount of a compound of claim 1 which is suitable for the alleviation of said condition.

* * * * *

UNITED STATES PATENT AND TRADEMARK OFFICE
CERTIFICATE OF CORRECTION

PATENT NO. : 5,346,916

DATED : September 13, 1994

INVENTOR(S) : Gèrald Guillaumet, Bèatrice Guardiola

It is certified that error appears in the above-indentified patent and that said Letters Patent is hereby corrected as shown below:

TITLE PAGE, Item [56] U.S. Patent Documents line 1; "BeBernardis" should read -- DeBernardis -- (Notice of References Cited U.S. Patent Documents dated 6-23-92)
Column  4, line 57; delete the "ps" at the end of the line.
Column 30, line  7; delete the "an" at the beginning of the line. (Prel. Amdt. 3-16-93)
Column 30, line 15; "$R_1$" should read -- $R_1O$ -- (Resp. and Amdt. dated 12-28-93)

Signed and Sealed this

Twenty-seventh Day of December, 1994

Attest:

BRUCE LEHMAN

Attesting Officer

Commissioner of Patents and Trademarks